US005552112A

United States Patent [19]

Schiffmann et al.

[11] Patent Number: 5,552,112
[45] Date of Patent: Sep. 3, 1996

[54] METHOD AND SYSTEM FOR STERILIZING MEDICAL INSTRUMENTS

[75] Inventors: Robert F. Schiffmann, New York, N.Y.; Jeffery S. Held, Chicago, Ill.

[73] Assignee: Quiclave, LLC, Chicago, Ill.

[21] Appl. No.: 381,685

[22] Filed: Jan. 26, 1995

[51] Int. Cl.$^6$ .................................... A61L 2/00
[52] U.S. Cl. ............. 422/21; 219/710; 219/712; 219/718; 219/759; 422/1; 422/105; 422/109; 422/307
[58] Field of Search ................. 422/1, 21, 38, 422/105, 109, 119, 186, 186.02, 186.06; 219/759, 730, 718, 762, 710, 712

[56] References Cited

U.S. PATENT DOCUMENTS

| | | |
|---|---|---|
| 3,261,140 | 7/1966 | Long et al. . |
| 3,311,287 | 3/1967 | Long et al. . |
| 3,961,569 | 6/1976 | Kenyon et al. . |
| 4,250,139 | 2/1981 | Luck et al. ............................. 422/21 |
| 4,316,070 | 2/1982 | Prosise et al. . |
| 4,362,917 | 12/1982 | Freedman et al. . |
| 4,398,077 | 8/1983 | Freedman et al. . |
| 4,415,790 | 11/1983 | Diesch et al. ......................... 219/712 |
| 4,503,307 | 3/1985 | Campbell et al. . |
| 4,558,198 | 12/1985 | Levendusky et al. . |
| 4,599,216 | 7/1986 | Rohrer et al. ......................... 422/21 |
| 4,614,514 | 9/1986 | Carr et al. ............................. 604/113 |
| 4,671,935 | 6/1987 | Rohrer et al. ......................... 422/21 |
| 4,786,773 | 11/1988 | Keefer ................................. 219/710 X |
| 4,808,782 | 2/1989 | Nakagawa et al. ................. 219/730 X |
| 4,808,783 | 2/1989 | Stenström .......................... 219/710 X |
| 4,861,956 | 8/1989 | Courneya .......................... 219/10.55 A |
| 4,933,525 | 6/1990 | St. Phillips ........................ 219/710 X |
| 4,952,420 | 8/1990 | Walters ................................. 427/97 |
| 4,956,155 | 9/1990 | Rohrer et al. ......................... 422/297 |
| 4,971,773 | 11/1990 | Rohrer et al. ......................... 422/307 |
| 5,019,344 | 5/1991 | Kutner et al. ......................... 422/21 |
| 5,019,359 | 5/1991 | Kutner et al. ......................... 422/294 |
| 5,039,495 | 8/1991 | Kutner et al. ......................... 422/299 |
| 5,061,443 | 10/1991 | Iijima et al. ........................... 422/21 |
| 5,184,046 | 2/1993 | Campbell ........................... 315/111.21 |
| 5,185,506 | 2/1993 | Walters ............................ 219/10.55 E |
| 5,217,768 | 6/1993 | Walters et al. ....................... 428/35.8 |
| 5,254,821 | 10/1993 | Walters ............................ 219/10.55 E |
| 5,256,846 | 10/1993 | Walters ............................ 219/10.55 E |
| 5,281,784 | 1/1994 | Kuhn . |
| 5,288,962 | 2/1994 | Lorence et al. . |
| 5,300,746 | 4/1994 | Walters et al. ......................... 219/745 |
| 5,413,757 | 5/1995 | Kutner et al. ......................... 422/21 |

OTHER PUBLICATIONS

"Microwave Sterilization," Michael D. Rohrer et al., JADA, vol. 110, pp. 194–198, (Feb., 1985).
"Endodontic Oburation Technique," author unkown, Clinical Research Associates Newsletter, vol. 13, Issue 9, pp. 1–4, (Sep., 1989).
"Sterilization, Rapid Steam Heat," author unknown, Clinical Research Associates Newsletter, vol. 16, Issue 4, pp. 1–2, (Apr., 1992).
"Glimpses Given on Two Products," Robert Stevenson, Focus on Ohio Dentistry, vol. 66, No. 5, (May, 1992).
"Introduction Picotron" advertisement published by Park Dental Research Corp. No Date Available.
"Ultraviolet/Ozone Generator for Sterilization of Medical and Dental Equipment," author unknown, published by East/West Technology Partners, Ltd. No date available.

(List continued on next page.)

Primary Examiner—Robert Warden
Assistant Examiner—Krisanne M. Thornton
Attorney, Agent, or Firm—Brinks Hofer Gilson & Lione

[57] ABSTRACT

A method of sterilizing an object having the steps of providing a container with an exterior surface that has a microwave interactive layer and defines an interior space having an initial temperature. An object is then placed within the interior space of the container. Next, the microwave interactive layer is exposed to a first amount of microwaves so that the layer produces heat which raises the temperature within the interior space to a predetermined sterilization temperature. The predetermined sterilization temperature is then maintained within the interior space for an amount of time sufficient to sterilize the object.

80 Claims, 10 Drawing Sheets

OTHER PUBLICATIONS

"Sterilization and Disinfection," Bernard L. Davis et al., source unknown, pp. 1452–1465. No date available.

"Theory of Induction Heating," author unknown, source unknown, pp. 11–21. No date available.

"Mitech Medical: Sterilizer Warms to World," Ellen Moffett, source unknown. No date available.

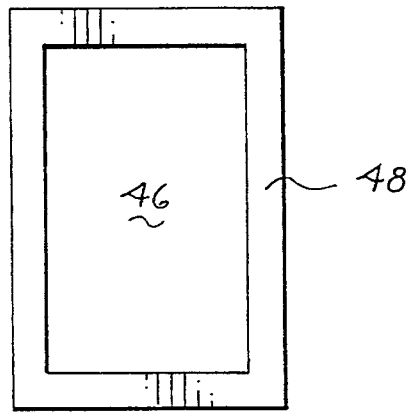
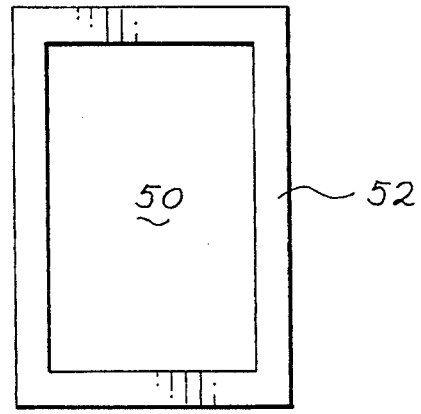
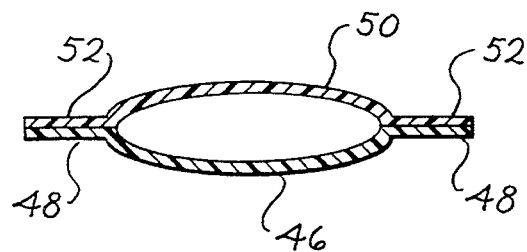
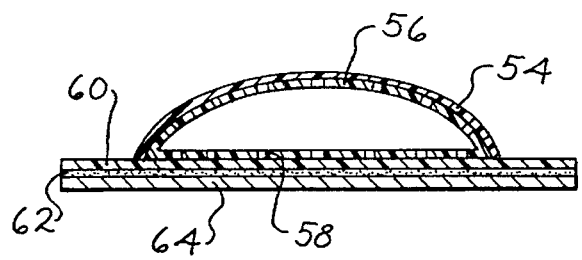
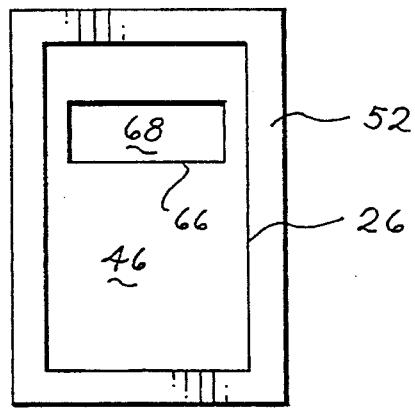
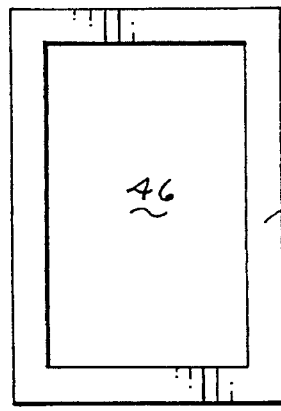

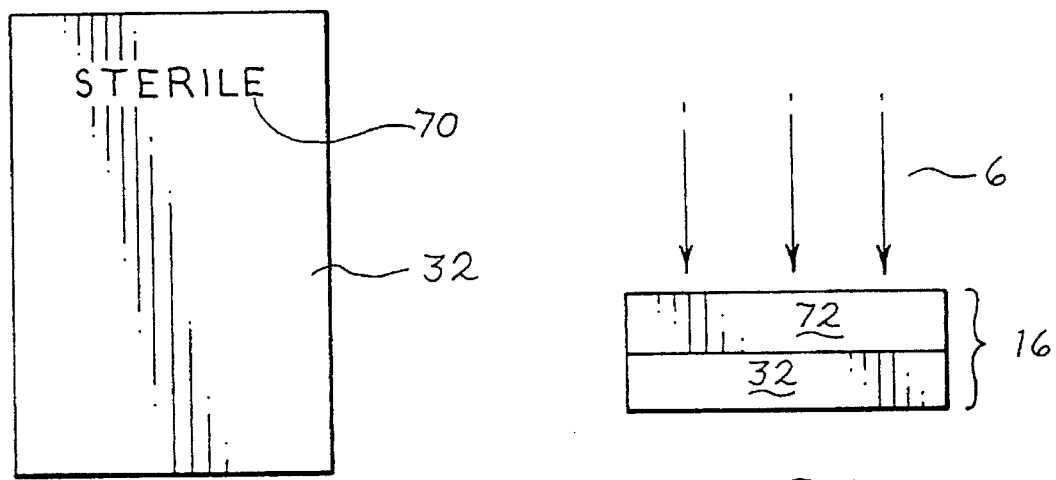
Fig. 11
Fig. 12
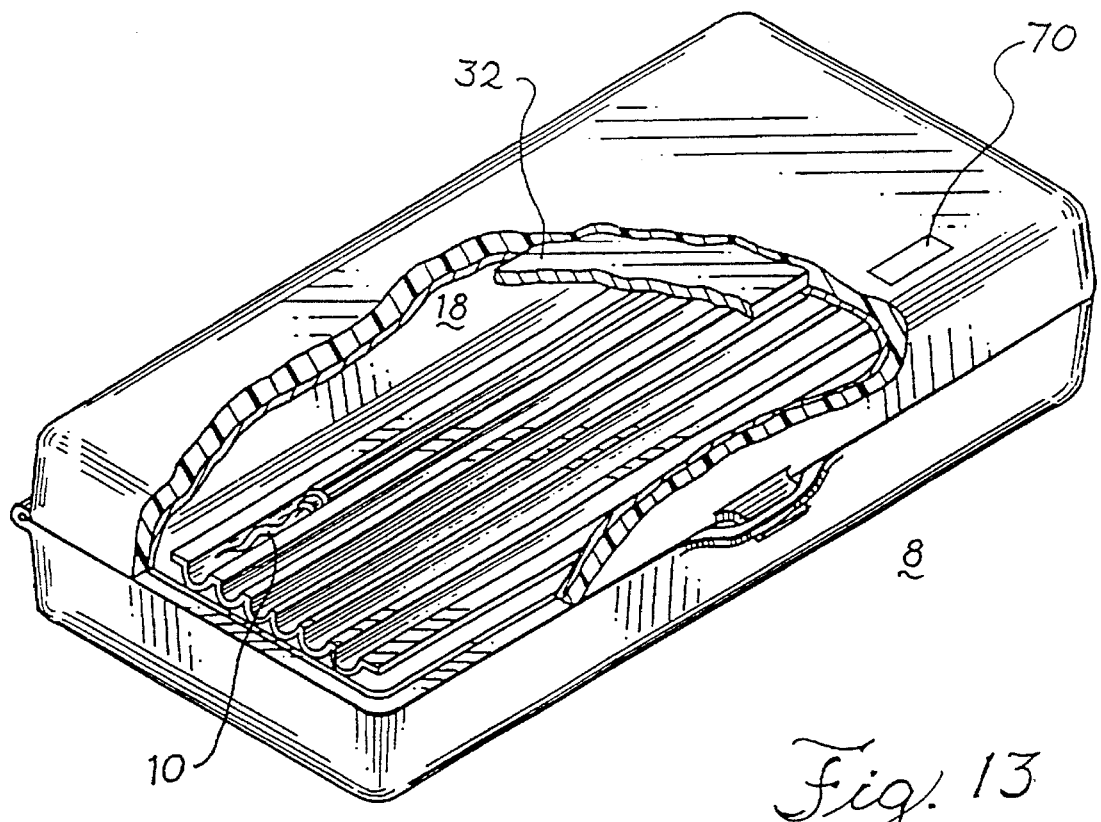
Fig. 13

METHOD AND SYSTEM FOR STERILIZING MEDICAL INSTRUMENTS

BACKGROUND OF THE INVENTION

1. Field Of The Invention

This invention relates to a method and system for sterilizing a metallic surgical instrument with microwave radiation and preventing arcing of the metallic surgical instrument.

2. Discussion Of Related Art

The constant exposure of dental and medical personnel and instruments to saliva and blood in virtually every dental and medical procedure is an ever present hazard and potential contributor to the transmission of infection. A variety of approved instrument sterilization methods are available. However, all methods have drawbacks in relation to surgical instruments or dental handpieces and burs.

The most commonly used method of sterilization, autoclaving, is damaging for almost all high-speed dental handpieces. In a study of dental handpieces claimed to be autoclavable, deterioration of performance was noted in a simulated 3-month period. Furthermore, autoclaving, without pretreatment in an oil emulsion, will destroy the sharp edge of burs.

A second method of sterilization is to apply heat to the instruments. This method has the drawback that temperatures of about 160° C. are required while heat generators to rapidly produce such temperatures are not commonly available. The method has further disadvantages in that the rubber and plastic washers and bushings within the dental handpieces could potentially be damaged and long exposure times (approximately 1 hour) are needed.

Gas sterilization with an ethylene oxide mixture is acceptable for both handpieces and burs. However, this is impractical because of cost of equipment, long sterilization and aeration times involved, and cost of providing adequate protection for personnel.

Alkaline glutaraldehyde (2%) will sterilize equipment, but it must be used for 10 hours to kill spore-forming organisms or tuberculosis microorganisms and is irritating to tissue. It must also be constantly monitored as it is not effective when it is more than 2 weeks old.

Another method of sterilization of medical instruments is to scrub them in a detergent solution and wipe them with alcohol. However, because of their serrated or rough handgrip surfaces, most instruments cannot be disinfected in this way. Except when dry heat is available, no practical method exists for sterilization of dental burs that will not quickly dull the cutting edge.

The above-described sterilization methods are not as advantageous as using dry heat to sterilize medical, dental and similar tools and instruments, because dry heat causes the least amount of damage, such as dulling or rusting to the tools. Dry heat sterilization requires the application of temperatures on the order of 130° C. to 170° C. for several minutes to destroy all pathogens including spore formers. Unfortunately, such techniques are slow when the tools are placed in hermetically sealed pouches since the heat transfer rate through a pouch is slow. Faster dry heat technology is available but it entails placing the tools in a perforated holder or open tray and using high velocity hot air to accomplish the sterilizing, after which the tools would be sterile but open to the air and subject to recontamination.

Microwave energy has been thought of numerous times in the past as a means of sterilizing materials including food products. However, when microwaves are used directly and indirectly to sterilize metallic tools and instruments, which are commonly used in the medical and dental professions, several problems are immediately apparent. The fact that the tools are metallic means they will be heated only slightly or not at all by the microwaves, unless they happen to be magnetic which is not common. This means an auxiliary heat source is required and that must be capable of direct interaction with the microwaves in order to produce heat which will, in turn, heat the tools and, thereby, sterilize them.

A second major problem which is common with any attempt to sterilize metallic tools or instruments is the production of arcs or corona discharge. This may occur between two tools in close proximity to each other or at the sharp edges, points or tips of a single instrument. Such an arc will actually melt the metal and destroy the usefulness of the tool.

Several approaches have been proposed to circumvent these two major problems. First, sterilization by the indirect application of microwaves has been disclosed in U.S. Pat. Nos. 5,019,344; 5,019,359 and 5,039,495. In those patents it is disclosed to use microwaves to vaporize a liquid sterilant solution and to expose the instruments to either the vaporized sterilant alone or to both the microwaves and the vaporized sterilant. When using microwaves to sterilize the instruments, the instruments are placed in a shielded and pressurized atmosphere produced by the vaporized sterilant. The pressurized atmosphere prevents arcing and aids in sterilizing the instruments in conjunction with the microwaves.

In another microwave sterilization technique, dental instruments are directly exposed to microwaves within a microwave oven. The instruments may be placed in plastic autoclave bags when exposed. This technique suffers from several shortcomings, such as (1) needing to rotate the objects in a three-dimensional manner within the oven to uniformly heat the instrument; (2) needing to shield the oven from energy not absorbed by the instruments that is reflected back to the oven; and (3) requiring either an absorber of microwaves, such as water, or an absorber of radar waves within the oven to prevent arcing.

One way to deal with this problem is to surround the tools with a microwave impervious but absorbent material which will prevent the microwaves from "seeing" the tools but will become hot by itself and transfer its heat to the tools. Such materials, which are often used to make such consumer microwave cookware as browner and pizza trays, are usually bulky and expensive and do not lend themselves to the manufacture of disposable pouches.

Another approach is to use disposable inexpensive materials commonly known as microwave susceptors which can be formed into flexible or rigid pouches or boxes. These are generally made by thin film deposition of metals such as aluminum or steel upon plastic films such as polyester. This, in turn, is usually bonded to paper or paperboard to provide support when heated with microwaves. Such films when exposed to microwaves may rapidly reach temperatures of 200° C. which would be useful for sterilization, however, they have a severe drawback for the application described—namely that they do not prevent arcing of metal objects. The reason is that they are largely transparent to the microwave energy and, thus, some microwaves will be received by a metal object. Though it is well known that microwaves reflect off metals, they actually penetrate the metal surface by about 1 μm. This slight penetration causes an activation of the surface electrons in a random manner and creates a current moving along the surface. If a potential charge builds up on a material to the level where it exceeds the ability of the air to carry away the charge, an arc will occur. It is well known that the build up of charge is particularly prevalent at sharp edges or points of the metal surface. When metallic tools, such as dental explorers, are placed in a pouch or box made of commonly available susceptor products and then heated in a microwave oven arcing will occur between tools in close proximity or at their sharp tips. A common occurrence will be a large bright flash almost immediately after the magnetron is energized. This may cause the susceptor to ignite and vigorously burn, while the sharp tip of the dental explorer will be melted into a ball making it useless. In addition, this arcing can damage the oven.

The inventors have addressed the problem of arcing in microwave susceptor containers by inventing a container structure that allows for sterilization of metallic objects while preventing arcing. The container structure is disclosed in U.S. patent application Ser. No. 08/319,944, filed Oct. 7, 1994.

SUMMARY OF THE INVENTION

The present invention concerns a method of sterilizing an object having the steps of providing a container with an exterior surface that has a microwave interactive layer and defines an interior space having an initial temperature. An object is then placed within the interior space of the container. Next, the microwave interactive layer is exposed to a first amount of microwaves so that the layer produces heat which raises the temperature within the interior space to a predetermined sterilization temperature. The predetermined sterilization temperature is then maintained within the interior space for an amount of time sufficient to sterilize the object.

Another aspect of the present invention concerns a system for sterilizing an object which has a microwave source that emits microwave radiation. A container is positioned so as to be exposed to the emitted microwave radiation. The container has an exterior surface having a microwave interactive layer and defines an interior space having an initial temperature. The interior space of the container has an object located therein. A microwave source controller controls the amount of microwaves that expose the microwave interactive layer so that the layer produces heat which raises the temperature within the interior space to a predetermined sterilization temperature which is maintained thereat for an amount of time sufficient to sterilize the object.

Each aspect of the present invention provides many advantages such as allowing one to inexpensively and quickly sterilize one or more metallic and nonmetallic dental and/or surgical instruments.

Each aspect of the present invention allows one to safely place a metallic object within a microwave source or oven without producing arcing problems.

Each aspect of the present invention allows one to use commercially available microwave susceptor containers to sterilize metallic instruments without fear of arcing.

The foregoing features and advantages of the present invention will be further understood upon consideration of the following detailed description of the invention taken in conjunction with the accompanying drawings, in which:

BRIEF DESCRIPTION OF THE DRAWINGS

FIGS. 9a–d show a third embodiment of a sterilization container with a viewing window according to the present invention;

FIGS. 10a–b show a fourth embodiment of a sterilization container with a viewing window according to the present invention;

FIG. 11 shows a top view of the embodiment of a sterilization container of FIG. 3 with a visual indicator;

FIG. 12 shows an embodiment of the layered structure of the exterior surface of the sterilization container of FIG. 3;

FIG. 13 shows a sterilization container in the form of a cassette according to the present invention;

FIG. 18b shows a plot of the power versus time to generate the temperature plot of FIG. 18a;

FIG. 19b shows a plot of the power versus time to generate the temperature plot of FIG. 18a;

DESCRIPTION OF THE PREFERRED EMBODIMENT

Figure 1:
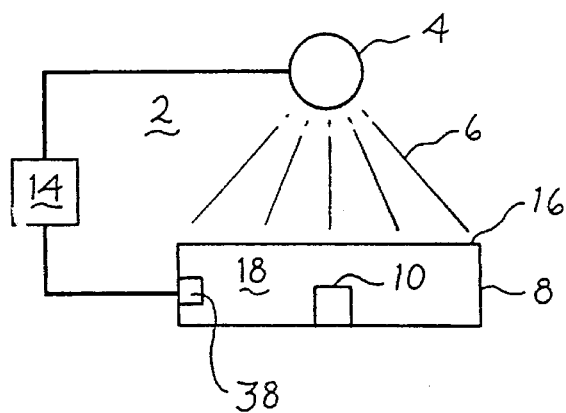
FIG. 1 schematically shows a system for sterilizing an object with microwave radiation according to the present invention.

Referring now to the drawings wherein like reference characters designate identical or corresponding parts throughout the several figures, and in particular FIG. 1 schematically shows a system for sterilizing an object. The sterilization system 2 includes a microwave source 4 which emits microwave radiation 6 towards a sterilization container 8 which contains an object 10. For the purpose of this application, microwaves are considered to be electromagnetic radiation having a frequency ranging from approximately $10^6$ Hz to approximately $3 \times 10^{11}$ Hz. It is preferred that the frequency of the microwaves is approximately 2,450 MHz, the frequency of most commercial microwave ovens.

Figure 2:
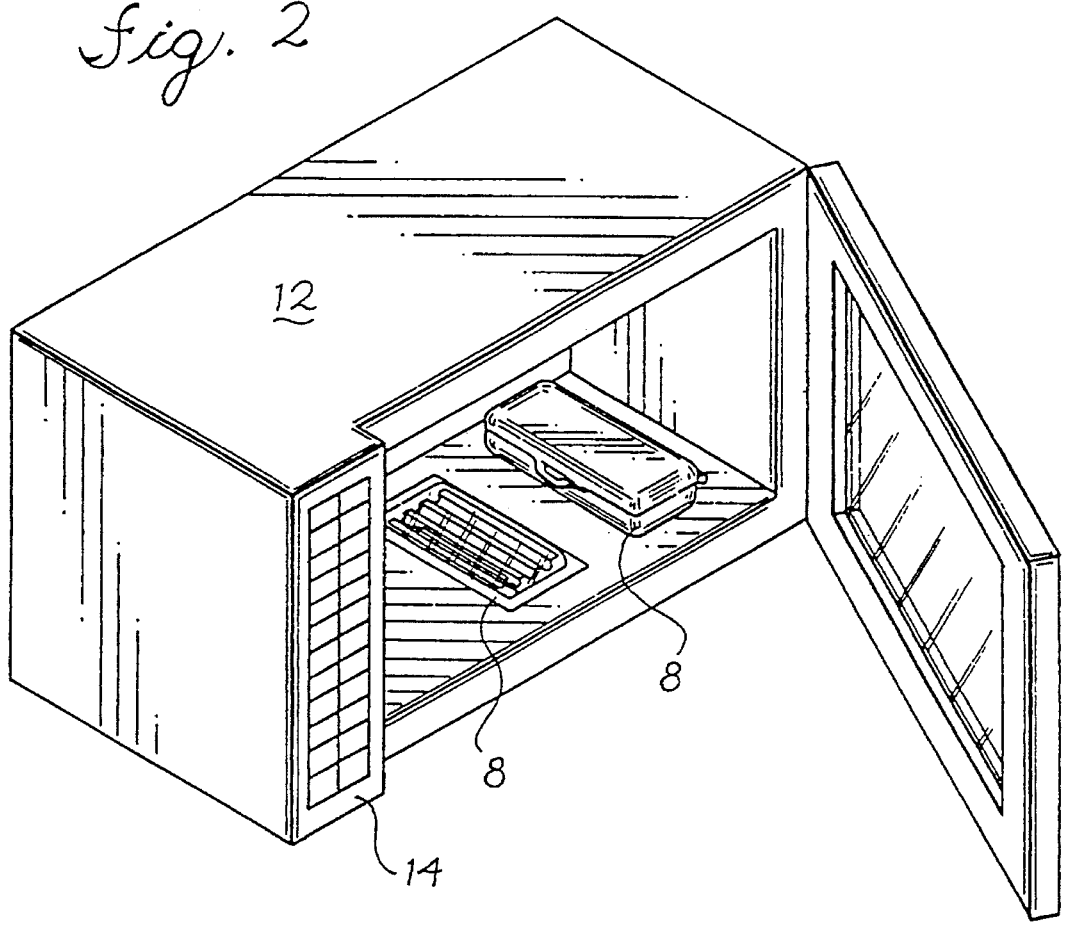
FIG. 2 shows both a sterilization bag and cassette containing a surgical instrument that are placed in a microwave device for sterilization according to the present invention.
Figure 3:
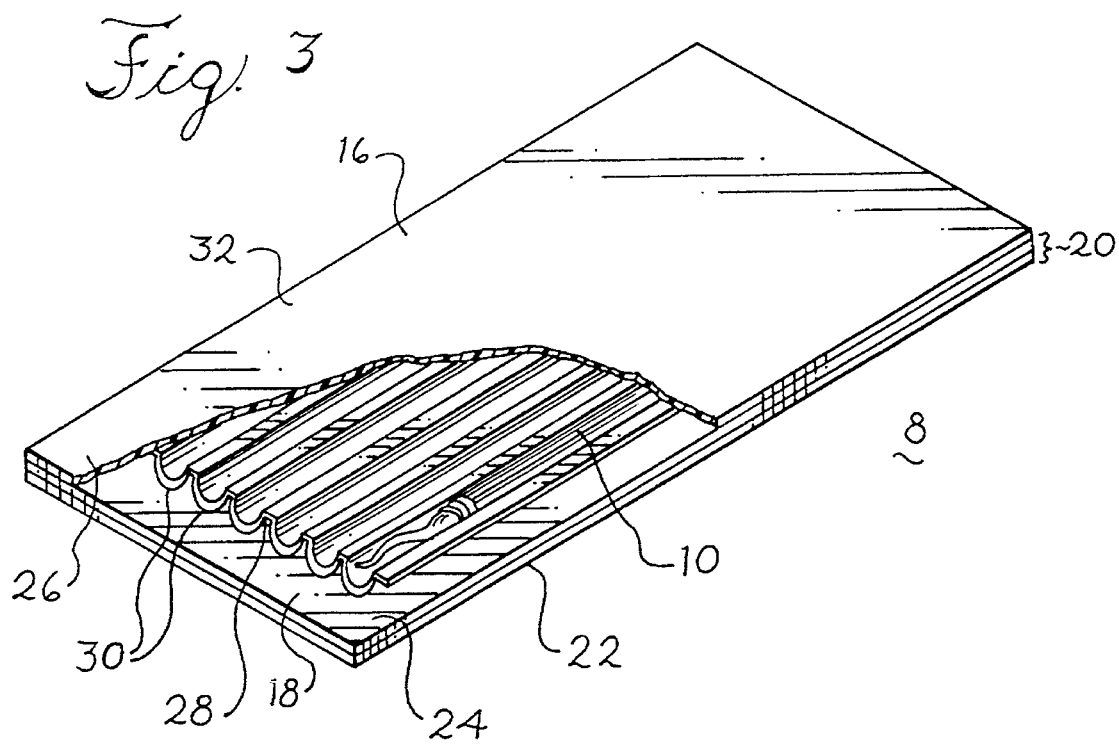
FIG. 3 shows a perspective, cut-away view of a first embodiment of a sterilization container according to the present invention.
Figure 4:
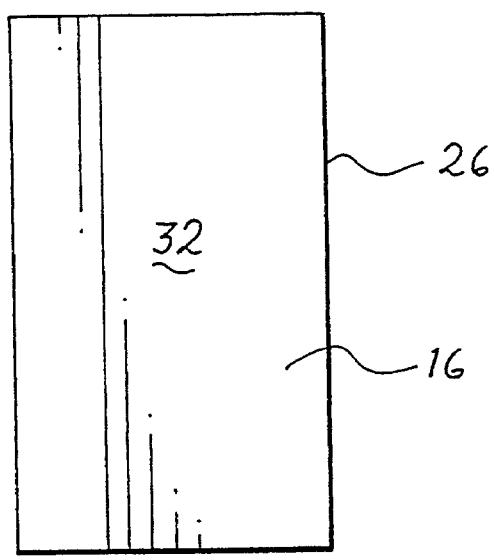
FIG. 4 shows a top view of the sterilization container of FIG. 3.

As seen in the embodiment of FIG. 2, microwave source 4 preferably is a microwave oven 12 which has a microwave source controller 14 which controls the amount of microwaves that are emitted by the oven 12 by controlling the power supplied to the oven 12. A sterilization container 8 is placed within the oven 12. As seen in FIGS. 3 and 4, container 8 has an exterior surface 16 which defines an interior space 18 into which the object 10 is placed. Container 8 preferably consists of a continuous surface having an inner surface defining interior space 18 into which the object 10 is placed. The continuous surface preferably has a bottom 20. The bottom 20 may be made of (1) a single material, such as a flexible aluminum foil or polyester, or (2) a dual layer structure with an exterior surface 22 and a support surface 24. Container 8 also has a top 26 attached to bottom 20. Top 26 may also have a dual layer structure like bottom 20 with or without a viewing window or patch.

Figure 5:
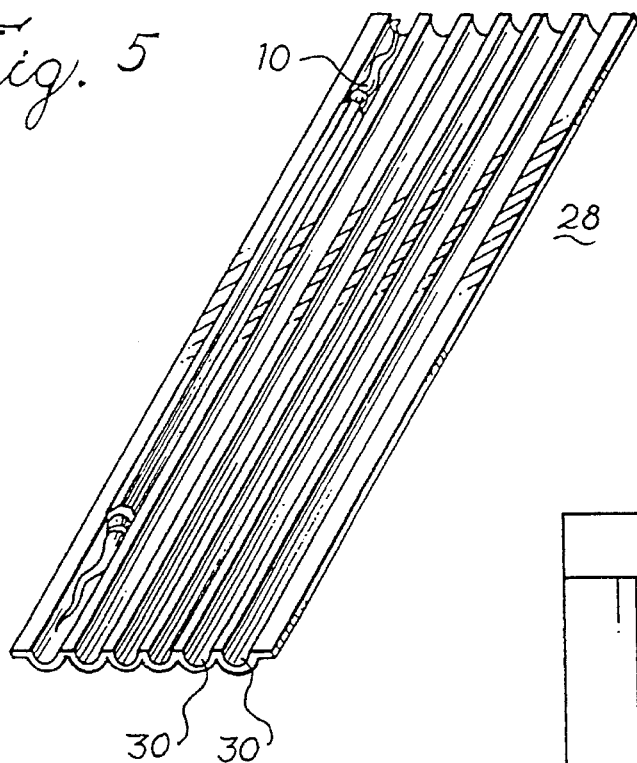
FIG. 5 shows a top perspective view of a tray to be used with the sterilization containers of FIGS. 3, 4, and 6–11.

Object 10 may be any material that needs to be sterilized. In particular, the object 10 may be entirely or partially metallic, such as a dental instrument or a medical instrument as shown in FIGS. 3 and 5. To help prevent arcing between metal surgical instruments placed in the interior space 18 of container 8, the instruments are preferably placed in one of the channels of tray 28 that is positioned on support surface 24. As seen in FIG. 5, tray 28 is rectangular in shape, is made of paper or plastic and has one or more rectangular or round channels or compartments 30 in which a single instrument is placed therein. By separating the instruments a sufficient distance from each other, the potential for arcing between the instruments is lessened.

Once the object 10 is placed within the interior space 18, the container 8 is hermetically sealed so that the object 10 will be in a dry environment when sterilized by oven 12. Hermetic sealing is accomplished by heat sealing the container 8 or using other suitable methods such as adhesive or tape. Hermetically sealing the object 10 within the container 8 ensures that the environment is not contaminated by viruses or the like within the volume of space. Furthermore, object 10 preferably is exposed to a dry environment within the sealed interior space 18 of container 8.

Sterilization of object 10 by the microwaves 6 emitted by oven 12 is accomplished by having container 8 convert the microwaves that impinge on its exterior surface 16 into heat. This heat is generated within the interior space 18 in an amount that is sufficient to sterilize the object 10. As seen in FIG. 4, substantially all of the exterior surface 16 of container 8 has a microwave interactive layer 32 which quickly converts some of the microwaves into heat. In addition, bottom 26 may also have a microwave interactive layer 32 to convert the microwaves into heat. An example of such a microwave interactive material is a microwave susceptor material which is well known and typically comprises a thin plastic layer with a plurality of metal (such as aluminum) conductive islands vacuum deposited therein. Examples of suitable susceptor materials are those known by the names of (1) ACCU.CRISP made by A.D. Tech of Tauton, Mass.; and (2) MICROCRISP by James River Corp. of Mentor, Ohio. The susceptor material may be either flexible or rigid, such as paperboard, so that the container 8 can be formed as either a pouch or cassette, respectively.

As described previously, if a susceptor material is used with a conventional microwave oven then metallic objects have a tendency to arc and melt since some of the microwaves 6 from the oven 12 are transmitted through the susceptor onto the object 10. Such conventional microwave ovens consist of a power supply, a magnetron, a launcher, a cavity with access door and a control panel. The magnetron tube usually operates at 100–120 volts and draws 10 to 15 amperes, and generates 400 to 1000 watts of microwave power which is launched into the cavity to heat objects therein. Many of these conventional ovens have a form of power output control which is able to reduce the average power into the cavity. Power reduction is nearly always done by pulsing the full power on and off over some duty cycle or time base, wherein a duty cycle or time base is defined to be the amount of time from beginning the pulsing of power to the time pulsing is completed. So, for example, in an 800 watt oven, it is possible to achieve an average output of 400 watts, or 50% power, by pulsing the full 800 watts on and off (assuming the pulse width is equal to half the pulse period). Since these time bases are long, typically 20 seconds or more, that means that the full 800 watts would be on for 10 or more seconds and cause the arcing problems described above.

In order to avoid the above arcing problems, the present invention recognizes that low microwave power needs to be generated throughout the heating/sterilizing cycle. The level of low microwave power needed ranges from about 1 Watt to about 400 Watts, preferably about 50 Watts to about 250 Watts. There are several ways to achieve stable continuous power without damage to the microwave source. One way is to use low wattage power output devices such as solid state transistors which can produce microwave power at ISM (Industrial, Scientific and Medical) frequencies such as 915 MHz. Another way is to use a standard microwave oven magnetron and modify the power supply so the magnetron is made to pulse on and off but does so at a very short time base—one second or preferably significantly less than one second so as to prevent the buildup of the electric field. To do this a separate filament transformer would be required. Another technique involves including a separate filament transformer in the power supply which can be used to control the anode plate current. There are other ways to accomplish the same controlled power reduction known to persons skilled in the art.

With the above-described modified oven it is possible to sterilize a metallic object 10 contained within a conventional susceptor material without the occurrence of arcing. Sterilization is accomplished by first exposing the microwave interactive layer 32 to a first amount of microwaves so that the layer 32 quickly produces heat which raises the initial temperature, $T_0$, within the interior space to a predetermined sterilization temperature, $T_S$, which ranges from about 175° C. to about 200° C. The predetermined sterilization temperature preferably is reached from about 30 to 60 seconds after the oven 12 is initially turned on. Once the predetermined sterilization temperature is reached, the power of oven 12 is controlled so that the temperature within the interior space 18 is maintained at the predetermined temperature for an amount of time sufficient to sterilize the object 10. Preferably, the object is exposed to the predetermined temperature for a time ranging from about 5 to 7 minutes. Examples of the temperature within the interior space 18 as a function of time are shown in FIGS. 17a, 18a, 19a, 20, 21 and 22a.

Figure 17A:
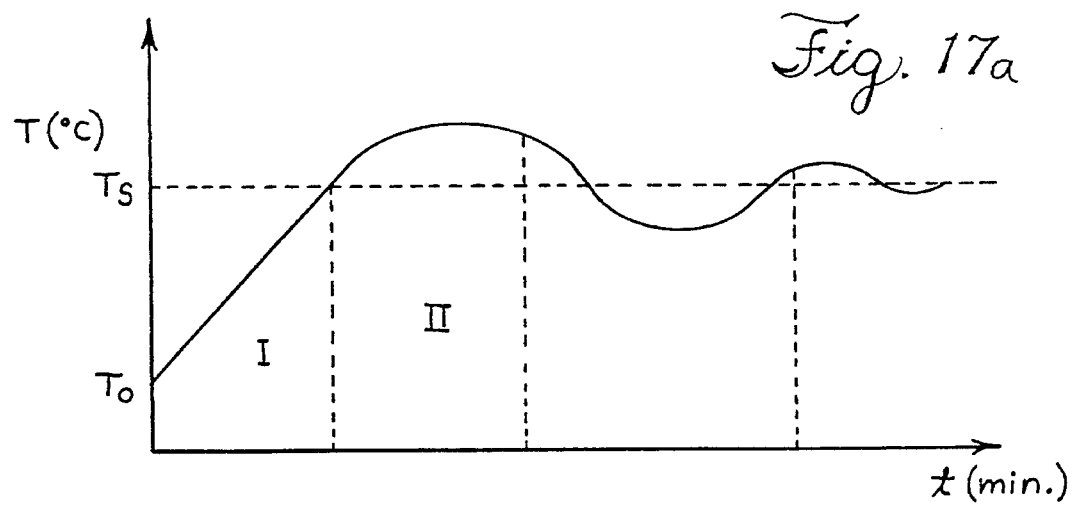
FIG. 17a shows a plot of the temperature within the interior of the sterilization containers of FIGS. 3–13 versus time when the power is applied in a non-pulse-like fashion according to the present invention.

The temperature curves of FIGS. 17a, 18a, 19a, 20, 21 and 22a are generated by controlling the power of oven 12 over time. As seen in FIG. 17a, there are two distinct regions for the temperature curve: Region I illustrates the initial exposure or power-up stage of the sterilization process and Region II illustrates the maintenance stage where the power is regulated so the temperature approaches a constant value.

During the initial exposure stage the temperature is raised in a linear manner from $T_0$ to $T_S$. This can be accomplished by running the microwave oven 12 at full power, such as 150 or 200 Watts, until $T_S$ is reached. This initial stage is graphically shown in FIGS. 17b, 18b and 21b. It is understood that there are other ways to power up the oven 12 so that the interior space quickly reaches the sterilization temperature, $T_S$, such as pulsing the power.

Once the sterilization temperature, $T_S$, is initially reached the temperature is ideally maintained there for a period of time that will ensure sterilization of the object. However, in real life maintaining a constant temperature is difficult to achieve due to the oven's inability to adjust the power quickly enough in response to the temperature within the interior space 18 of the container 8. Consequently, what occurs when the sterilization temperature is achieved is that the temperature will rise above that level. After it is sensed that the temperature is above $T_S$ the power is reduced so that the interior space 18 will cool down. The temperature in the interior space 18 decreases until it falls below $T_S$. The power is then increased so that the temperature will climb toward $T_S$. As seen in FIGS. 17a, 18a, 19a, 20, 21 and 22a, this process results in the temperature oscillating about the sterilization temperature, $T_S$, until the object 10 is sterilized.

Figure 14:
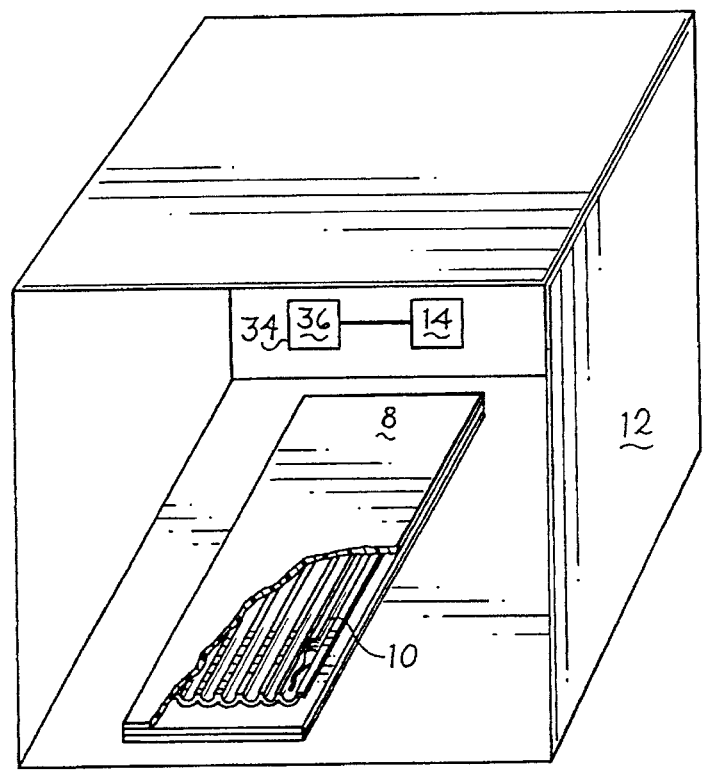
FIG. 14 shows an exterior sensor system to be used with the sterilization containers of FIGS. 3–13.

To monitor when the sterilization temperature is reached a temperature sensor 34 is employed. In one embodiment, temperature sensor 34 consists of an infrared temperature monitor 36 mounted to an interior wall of oven 12 as seen in FIG. 14. Temperature monitor 36 is electrically connected to microwave source controller 14. Temperature monitor 36 monitors the infrared energy emitted by the surface of container 8 or of an instrument 10 through a visual window or patch of container 8 and produces a signal representative of the temperature within the interior space 18 of the container 8. The signal is then relayed to microwave source controller 14 where the power of the oven 12 is controlled so that the temperature remains essentially constant within the interior space 18 of the container 8.

Figure 15:
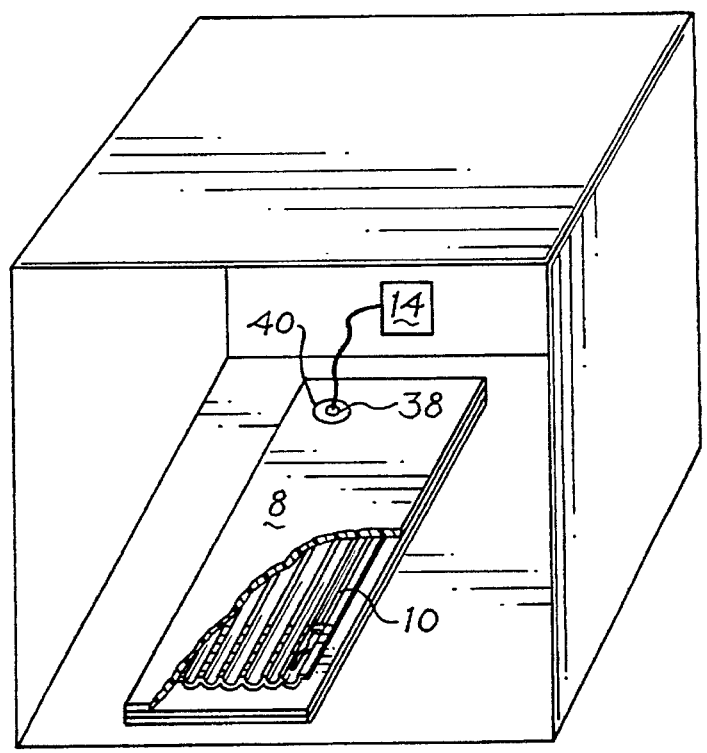
FIG. 15 shows an interior sensor system to be used with the sterilization containers of FIGS. 3–13.
Figure 16:
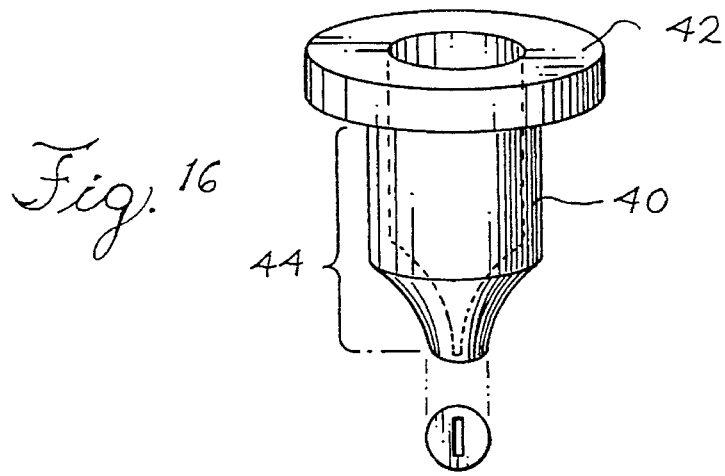
FIG. 16 shows an embodiment of a hermetic valve to be used with the interior sensor system of FIG. 15.

In a second embodiment, the temperature sensor 34 may be placed within the interior space 18 of container 8. An example of an interior sensor would be either a fiber-optic or fluoroptic temperature probe 38 electrically connected to microwave source controller 14, as seen in FIG. 15. Since probe 38 would actually be within the container, this embodiment requires that the container 8 be sealed immediately following removal of the temperature probe after sterilization of the object is complete. Alternatively, as shown in FIG. 16, a simple hermetic valve 40 through which the probe 38 may be inserted and withdrawn, which will maintain sterility. The valve 40 preferably has an annular opening 42 and a tapered end 44 made of silicon rubber or other flexible elastic material. The tapered end 44 is inserted into a slit made in the top 26 of the container 8 and then a probe 38 is inserted into the valve 40 and placed into the interior space 18 of container 8. Once the valve 40 and probe 38 are withdrawn from the interior space 18, the slit closes so that the container 8 remains hermetically sealed.

In either embodiment of the temperature sensor 34 shown in FIGS. 14 and 15, the temperature sensor 34 sends a signal to the microwave source controller 14 which controls the power of the oven 12 and, thus, the amount of microwaves emitted to and absorbed by the container 8. In one embodiment seen in FIGS. 17 a–b, when temperature sensor 34 initially senses a temperature corresponding to the predetermined sterilization temperature, $T_S$, a signal representative of the temperature is sent to controller 14 which then reduces the power of the microwave oven 12 to approximately 100 Watts so as to maintain the predetermined temperature within the container 8. When the temperature starts to rise above $T_S$ by approximately 5° C. the power is again reduced to about 75 Watts so that the temperature will fall back towards and below $T_S$. Eventually the temperature will rise above $T_S$ again which will precipitate a second reduction in power. As seen in FIGS. 17 a and b, these step reductions in power are continued until the temperature within container 18 has a nearly constant value of $T_S$. As seen in FIG. 17a, this rising and falling of the temperature resembles a sinusoidal curve with an exponentially decreasing amplitude.

Another way to control the temperature is shown in FIGS. 18 and 19 where the power is pulsed in region II so as to maintain the predetermined sterilization temperature. In this mode of operation the parameters of the pulsed power are controlled in response to the temperature sensed within the container 8 by sensors 34 placed either within or outside the container 8. Thus, the pulse period, pulse width, the frequency of the microwave radiation or all three in combination can be varied to maintain the temperature within the container 8. In this method the period of the pulsed power ranges from about 1/30th of a second to about 20 seconds, preferably 1 to 5 seconds; the pulse width of the pulsed power ranges from about 1/60th of a second to about 10 seconds, preferably 0.5 seconds to 2.5 seconds; and the frequency of the pulses ranges from about 1 MHz to about 10 GHz, preferably 100 MHz to 6 GHz.

FIGS. 18 a and b show a method of pulsing where the power is alternatively pulsed on at full power, such as 200 Watts, and then off. As one can see, when the temperature begins to fall below $T_S$ a pulse is generated at full power until $T_S$ is reached where the pulse is turned off. This results in the temperature rising above $T_S$. The next pulse is generated when the temperature falls below $T_S$ again. As before, once $T_S$ is reached the pulse is discontinued. This process is continued for approximately 5 to 7 minutes until the object 10 is sterilized. As with the method of FIGS. 17 the temperature eventually reaches equilibrium near $T_S$. Furthermore, as the temperature settles near $T_S$ the pulse width decreases while the pulse period may remain the same or change as well. The pulse width can decrease from a maximum width of approximately 20 seconds to a final width of approximately 1 second.

Figure 18A:
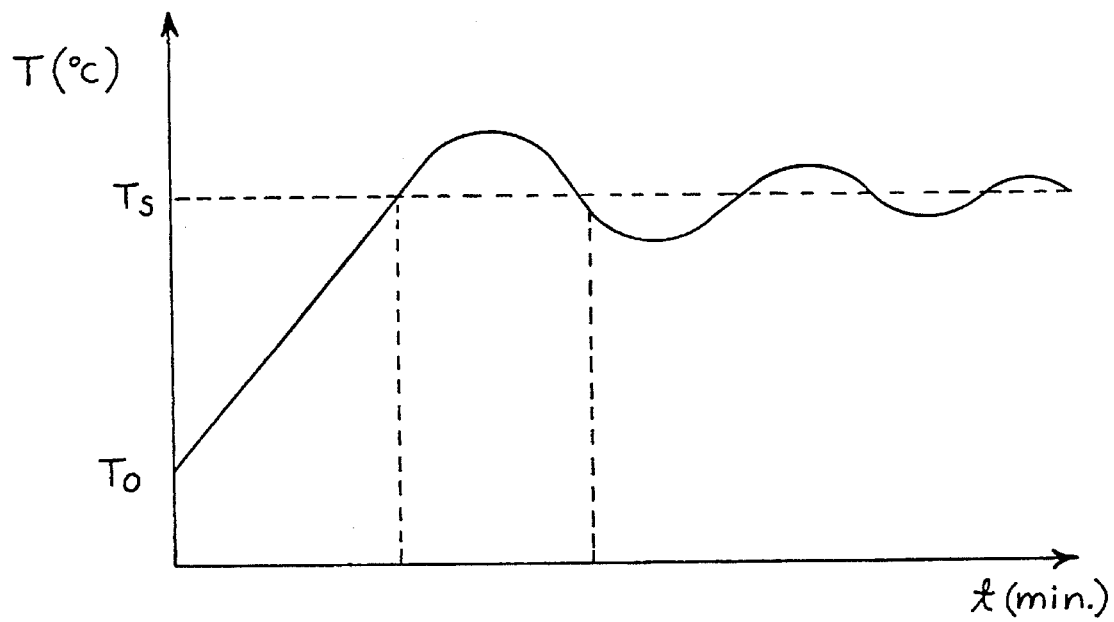
FIG. 18a shows a plot of the temperature within the interior of the sterilization containers of FIGS. 3–13 versus time when the power is pulsed on and off at full power according to the present invention.
Figure 18B:
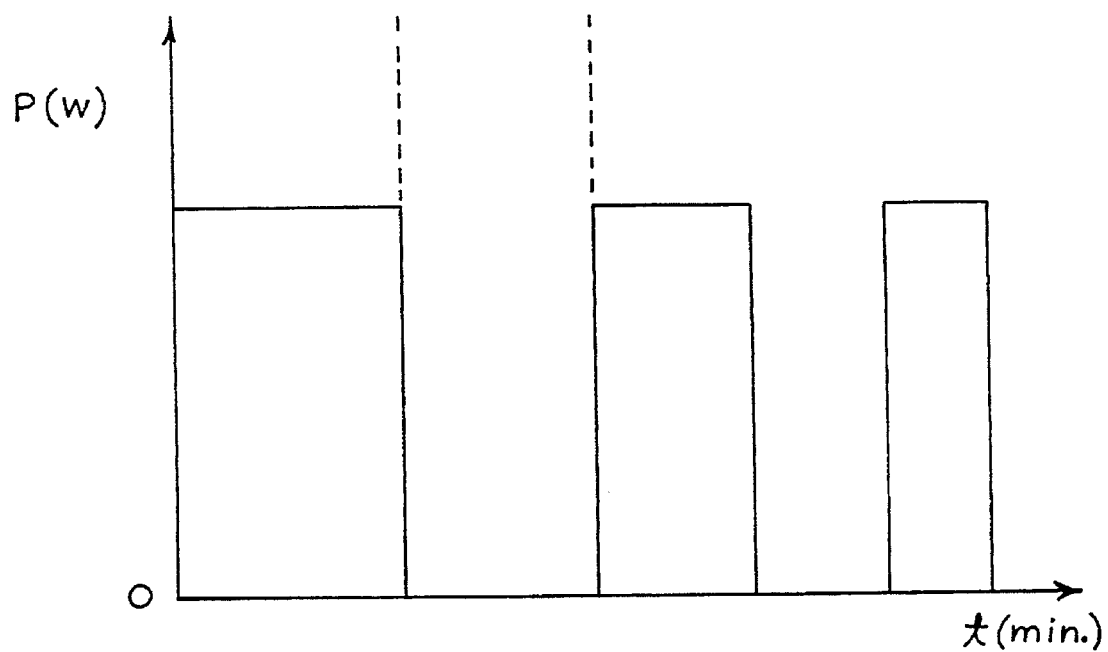
Figure 19A:
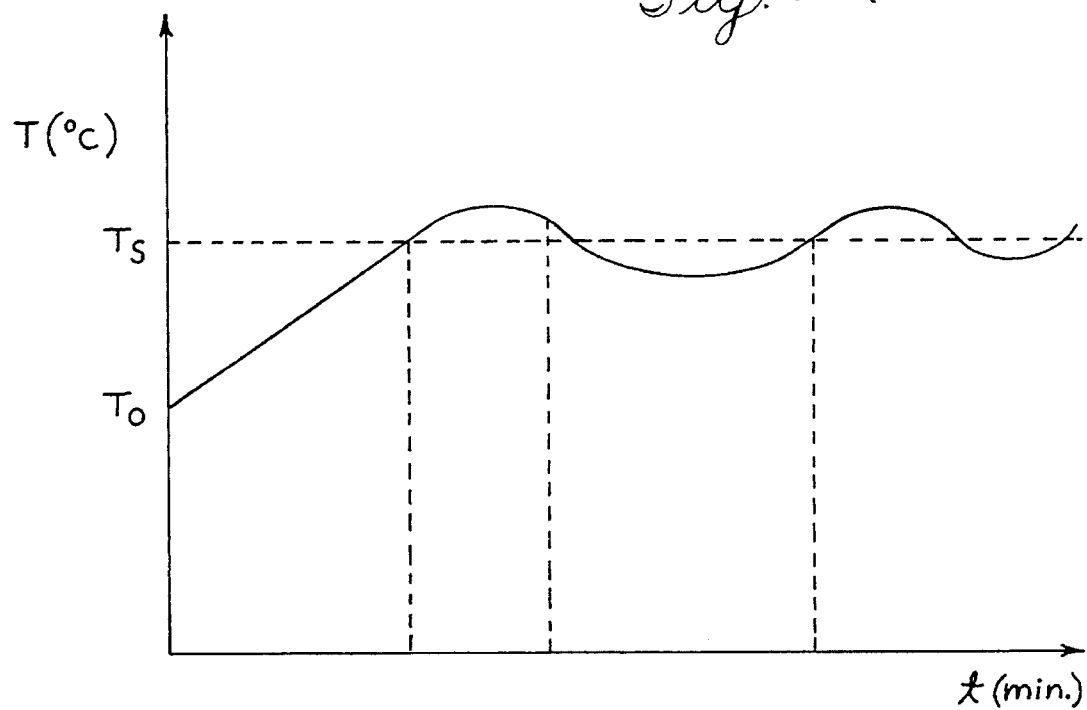
FIG. 19a shows a plot of the temperature within the interior of the sterilization containers of FIGS. 3–13 versus time when the power is pulsed on and off at reduced power according to the present invention.
Figure 19B:
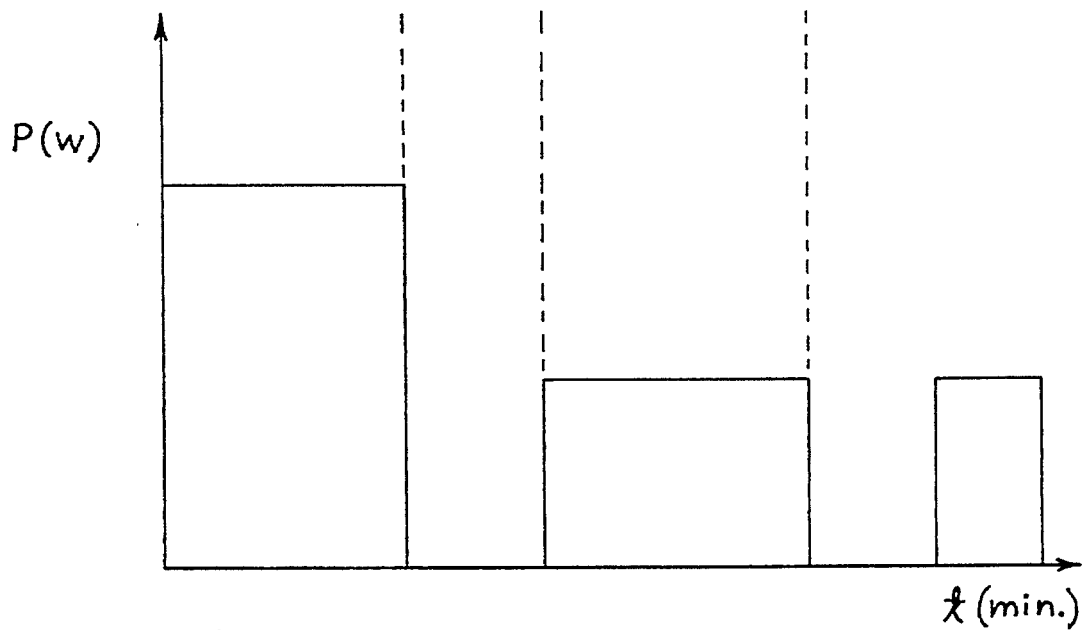

In another method shown in FIGS. 19a and b, the pulses are generated at a power which is significantly less than the oven 12 can generate at full power. In addition, the pulses are triggered on and off in a manner similar to that described above with respect to the method of FIGS. 18a and b. In the method of FIGS. 19a–b, oven 12 is set at full power of 200 Watts and the pulses will be generated at a power ranging from about 50 Watts to about 100 Watts. As one can see when comparing the methods of FIGS. 18 and 19, the pulses in the method of FIG. 19 have a greater width, approximately 2 times, than the pulses generated in the method of FIG. 18. This leads to the temperature within container 8 reaching equilibrium near $T_S$ more quickly than in the method of FIG. 18. Equilibrium is reached more quickly because the swings in temperature about $T_S$ are not as great which leads to needing less microwave power for each pulse. This reduction in pulse power allows for greater control of the microwave radiation emitted by the oven 12.

The end result of either method of controlling the power and temperature is that the object 10 is sterilized. Furthermore, if a metallic object 10 is present within container 8 the metallic object 10 does not arc, spark or otherwise exhibit corona discharge during either of Regions I and II shown in FIGS. 17–19.

As an illustration of the method and system described above, see the following two experimental examples.

EXAMPLE 1

A pouch was made from a sample of a flexible susceptor obtained from James River Corporation (Milltown, Ohio). The pouch was approximately 6 inches long and 3 inches wide and the seams were sealed with masking tape. A single dental explorer was placed in the pouch or container and the pouch was sealed with masking tape. The pouch was then placed in a Hirst MicroAire microwave oven manufactured in England and having a power supply which allows the operator to vary the power smoothly from 25 to 2000 watts. In this test the oven was first set at a frequency of 2,450 MHz and a power output of 800 watts as measured into a 1000 ml water load. The oven was energized and there was brilliant flash and the pouch began to burn. The fire was extinguished and the explorer removed from the pouch—the tip was completely melted into a ball and the instrument scorched.

A second pouch or container was prepared with a new dental explorer following the steps outlined above. However, this time the power of the Hirst oven was adjusted downwardly to 150 watts. Now when the oven was energized there was no flash or fire and the susceptor became hot. The microwave oven was shut off after 60 seconds and the pouch removed from the oven and the explorer was examined and it was in perfect condition.

EXAMPLE 2

Following the procedures described in Example 1, a dental explorer and a hand tool used for dental drilling were placed in a susceptor pouch along with spore strip biological indicators which were placed into the hand tool end or taped to the tools. The tools were placed in extremely close proximity. A small slit was made in the pouch and a fiber-optic temperature probe inserted into the pouch. The Hirst microwave oven was set at 2,450 MHz and energized at 150 watts output. The temperature inside the pouch was monitored on a model 750 Luxtron Fluoroptic Thermometer. The temperature rapidly reached 375° F. (191° C.) and then the power was shut off manually and restarted within a few seconds in order to maintain the temperature within the pouch in the range of 350° to 375° F. (177° to 191° C.). This was repeated for 7 minutes, effectively cycling the temperature in the range desired. After this the pouch and its contents were removed from the oven, the temperature probe removed from the pouch and the slit sealed with masking tape. The pouch was sent to a qualified microbiology laboratory which analyzed the spore strips and reported that a 6 log sterility had been achieved. No arcing or damage to the metallic tools occurred as well.

As a second step, the same test was repeated but using a susceptor box of approximately the same dimensions but made from a rigid susceptor sample received from the James River Corporation. Similar results were obtained when following the same test procedure described for the pouch.

Besides exposing the container 8 solely to microwave radiation, it is possible to simultaneously expose the container 8 and the object 10 within microwave oven 12 to both microwave energy and hot air. This heating combination has several advantages over using microwaves alone:

1. When exposing the container 8 and object 10 solely to microwaves, heat is created only by the microwaves interacting with the susceptor which, in turn, heats the air which then heats the object 10. Since the container 8 is of relatively low mass and the air in the microwave oven 12 is cold, the container tends to lose much of its heat to the air.
2. By using hot air in combination with the microwave energy the air inside the container 8 and the objects 10 therein are heated faster. The container 8 loses little of its heat to its surroundings and, hence, the objects 10 are heated faster and more efficiently.
3. Since the temperature of the hot air is at or near that of the container 8 and its contents it is easier to maintain the temperature inside the container near the predetermined sterilization temperature, $T_S$. For example, if the air within oven 12 is at the sterilization temperature, $T_S$, such as 375° F. (191° C.), little or no microwave energy may be required once the initial heating to the sterilization temperature has been accomplished. If the air within oven 12 is at a temperature slightly below the sterilization temperature, such as 325° F. (163° C.), then once the sterilization temperature is achieved within container 8 it can be maintained with low levels of microwave energy, either continuous or pulsed. However, the swings of temperature above and below the desired sterilization temperature will be narrowed as will be seen in the illustrations and examples below.
4. A possible reason for using an oven temperature slightly below that for sterilization is if the sensing of temperature is done based upon the surface temperature of the container, a temperature which is measured to be different than the oven temperature must be due to the temperature within the pouch.
5. Another advantage of hot air/microwaves is that it facilitates the sterilization of large medical instruments. Since the actual heat produced by the susceptor, which is of a very low thermal mass, would ordinarily be too small to heat a large mass of instruments alone, adding hot air would supplement the microwave generated heat and aid in the sterilization of large instruments which need to be subjected to larger heat quantities for sterilization to occur.

As an illustration of the method described above, see the following three experimental examples recited below:

EXAMPLE 1

Figure 17B:
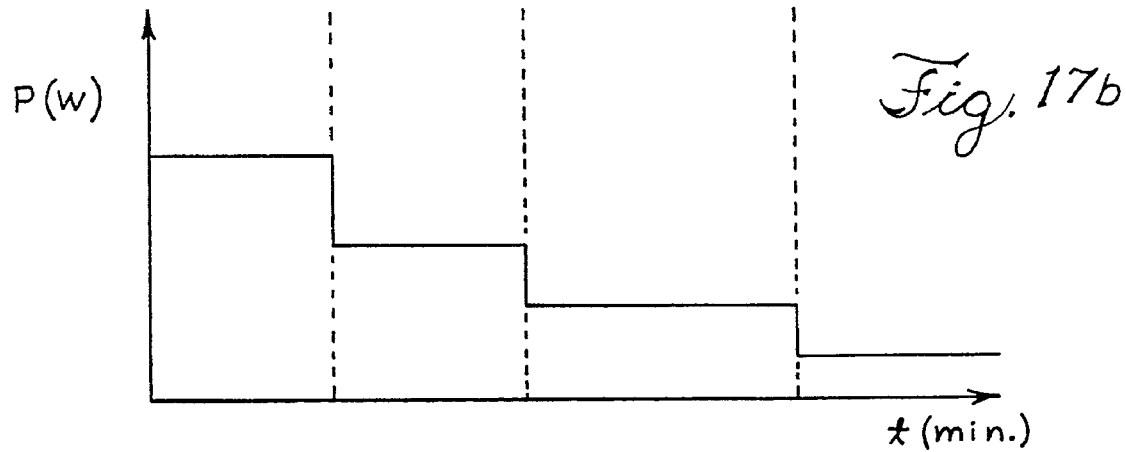
FIG. 17b shows a plot of the power versus time to generate the temperature plot of FIG. 17a when the temperature within the oven is initially at ambient temperature.
Figure 20:
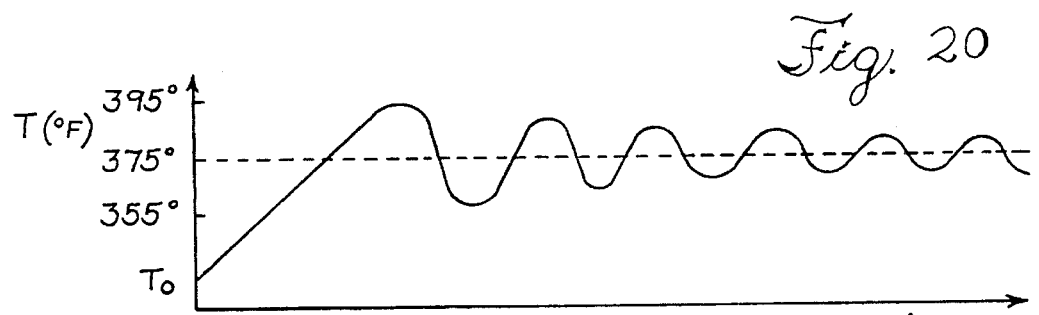
FIG. 20 shows a plot of the temperature within the interior of a sterilization container versus time when the temperature within the oven is at ambient temperature according to the present invention.

A flexible rectangular pouch or container with dimensions of 6"×3" was prepared from an aluminum microwave susceptor. A dental explorer inoculated with spore forming bacteria was placed therein and the pouch was sealed with masking tape. A Luxtron temperature probe was placed inside the pouch, through a small slit made in the pouch. The pouch was placed in a Hirst MicroAire oven which had been adjusted to a microwave power output of 175 watts at 2,450 MHz. The air in the oven was at the ambient temperature of 70° F. (21° C.). The oven was energized and the temperature monitored. The temperature inside the pouch reached 350° F. (177° C.) in approximately 35 seconds. The power was then pulsed on and off at full power to maintain an average temperature of 375° F. (191° C.). As seen in FIG. 20, temperature swings ranged from 355° F. to 390° F. (179° C. to 199° C.) for the first 3 or 4 minutes of heating; after that the range narrowed to 365° F. to 385° F. (185° C. to 196° C.). The microwave energy was shut off after 7 minutes, the sample was sealed with masking tape and sent to a qualified microbiology laboratory. A 6 Log reduction in microorganisms was achieved and no arcing or damage to the metallic instrument occurred. It is understood that the above method could be performed in a non-pulse-like fashion as shown in FIG. 17*b* or in a reduced power pulse-like fashion as shown in FIG. 19*b*.

EXAMPLE 2

Figure 21:
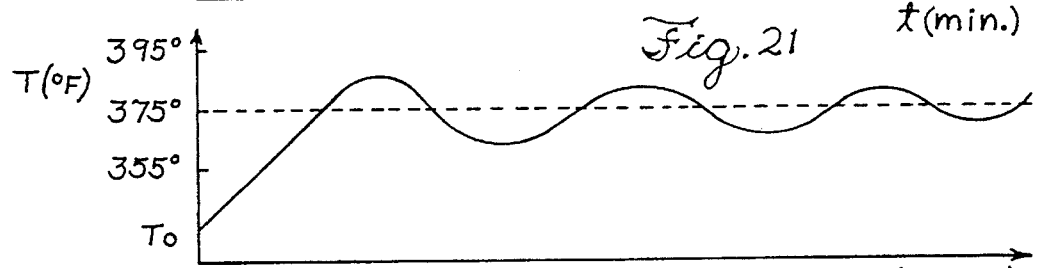
FIG. 21 shows a plot of the temperature within the interior of a sterilization container versus time when the temperature within the oven is below the predetermined sterilization temperature according to the present invention.

The above experiment was repeated, however, the oven was preheated to 300° F. (149° C.). The microwave oven 12 was energized as before and the container 8 reached an internal temperature of 350° F. (177° C.) in 25 seconds. The power was then pulsed on and off at full power over a seven minute period. As seen in FIG. 21, the average temperature of 375° F. (191° C.) was easier to maintain and generally ranged between 365° F. to 385° F. (185° C. to 196° C.), narrowing to 370° F. to 380° F. ( 188° C. to 193° C.) during the last few minutes. Once again a 6 Log reduction in microorganisms was achieved and no arcing or damage to the tools occurred. It is understood that the above method could be performed in a non-pulse-like fashion as shown in FIG. 17*b* or in a reduced power pulse-like fashion as shown in FIG. 19*b*.

EXAMPLE 3

Figure 22A:
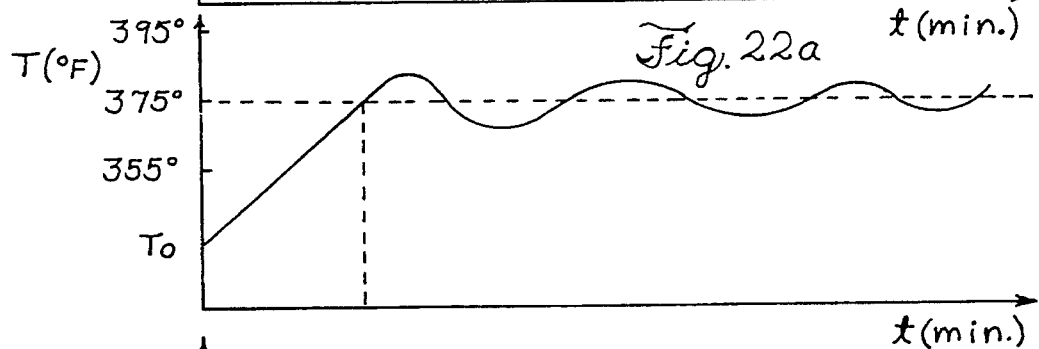
FIG. 22a shows a plot of the temperature within the interior of a sterilization container versus time when the temperature within the oven is at the predetermined sterilization temperature according to the present invention.
Figure 22B:
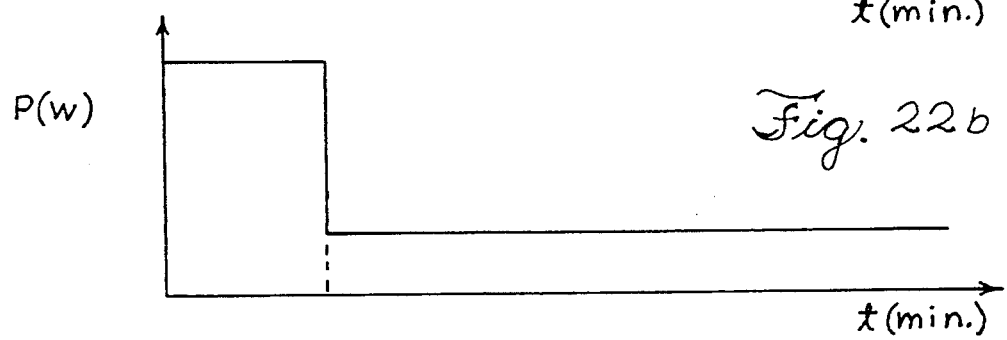
FIG. 22b shows a plot of the power versus time to generate the temperature plot of FIG. 22a when the power is applied in a non-pulse-like fashion according to the present invention.
Figure 22C:
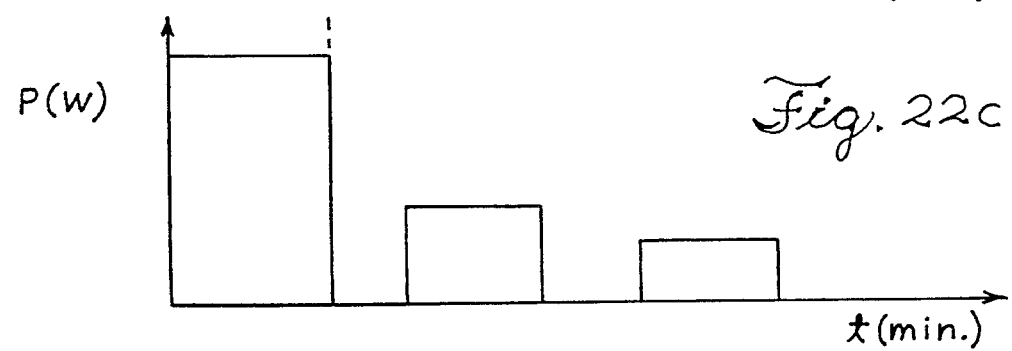
FIG. 22c shows a plot of the power versus time to generate the temperature plot of FIG. 22a when the power is pulsed on and off at reduced power according to the present invention.

As seen in FIGS. 22*a–c*, the test described in Example 2 was repeated, however, the oven 12 was first preheated to the predetermined sterilization temperature of 375° F. (191° C.). The microwave oven 12 was energized as before and the container's internal temperature reached 350° F. (177° C.) in about 25 seconds. As seen in FIG. 22*c*, when the temperature reached 375° F. (191° C.) the microwave oven 12 was shut off and then pulsed on and off at a reduced power of approximately 85 Watts for about one minute until a stable internal temperature of 375° F. (191° C.) was maintained. After 7 minutes the oven 12 was shut off and the sample removed. When analyzed a 6 Log reduction of microorganisms was achieved. Again no arcing or damage to the tools occurred. Note that the triggering of the pulses of Examples 1–3 was essentially the same as the triggering described for the methods shown in FIGS. 18–19.

It is understood that other ways of controlling the power are possible, like the non-pulse-like powering shown in FIG. 22*b* where the power is stepped down from an initial power of 200 Watts to a final power of 50 Watts. Though one step down in power is shown, it is possible that a plurality of steps down in power may be needed such as shown in FIG. 17*b*, and after a short time no more microwave power may be required.

Figure 6:
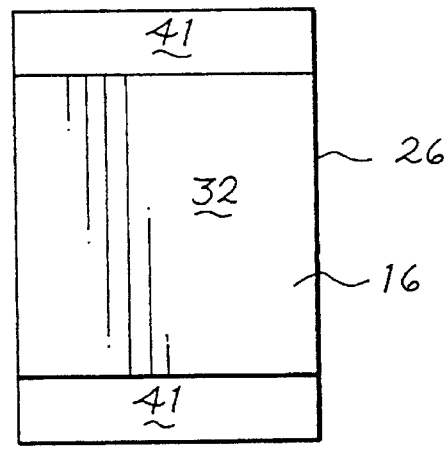
FIG. 6 shows a top view of a second embodiment of a sterilization container according to the present invention.

While the above examples and discussion describe the present invention when using a container 8 which is totally made of a susceptor material, other structures for container 8 are possible. For example, as shown in FIG. 6, only the central portion of the container 8 is made of a microwave interactive layer 32 while the end portions 41 are made of a foil or a foil laminated to paper or paperboard in order to prevent puncture of the surface of the container and to prevent the formation of a hot spot due to the proximity of a point of a sharp metal object 8 to the layer 32.

As seen in FIGS. 7–10 it is also possible to design a container in which the object 10 which is sterilized can be seen in the visual or infrared spectrum without opening the container 8. It would be an advantage to have an optically transparent window in the container in order that the dental or medical technician be able to see the instruments contained therein. Another reason is that, if the window material is chosen to be transparent to infrared, then an infrared sensor could monitor the surface temperature of the instruments or another object inside the container without invading the hermetic seal.

Figure 7:
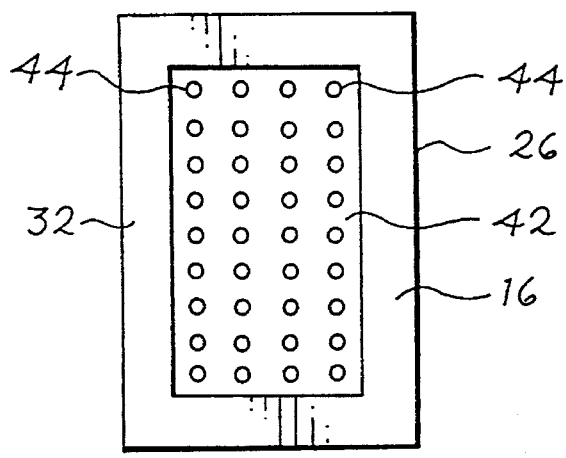
FIG. 7 shows a top view of a first embodiment of a sterilization container with a viewing window according to the present invention.

In FIG. 7 a susceptor container has a central see-through patch 42 made of a foil with a plurality of holes 44 of such dimensions to act as waveguide-beyond-cutoff and thereby permit the transmission of light out of the container 8 without the transmission of microwave power therethrough as well.

Figure 8:
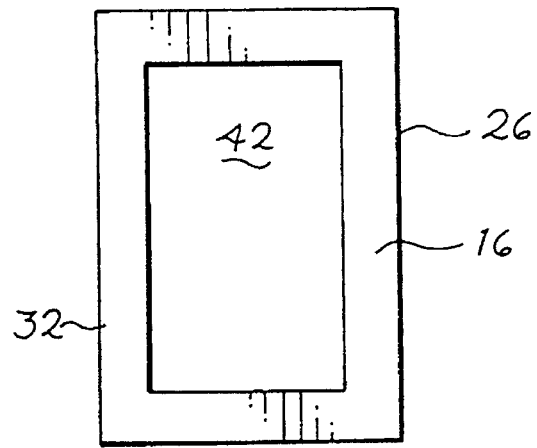
FIG. 8 shows a top view of a second embodiment of a sterilization container with a viewing window according to the present invention.

In a second embodiment shown in FIG. 8, the central see-through patch 42 may be made of a clear plastic film such as polyester, capable of withstanding the heat of contact with the susceptor, or otherwise thermally insulated from the susceptor. Such a window would be allowed providing that the microwave oven power was kept low enough to prevent arcing. In general, the second embodiment pertains to a container having two surfaces, each with an exterior surface and an inner surface. Both inner surfaces face each other and define a volume of space into which the metal object is placed. One or more of the surfaces is made of a microwave interactive layer, like a susceptor material, that absorbs microwave radiation impinging on an exterior surface of the container and converts the absorbed microwave radiation to radiant heat energy. In addition, one or more of the surfaces has an optically transparent material capable of withstanding temperatures of at least 400° F. (204° C.). Two examples of the second embodiment of the see-through patch 42 are given below.

EXAMPLE 1

As shown in FIG. 9*a*, a rectangular sheet of susceptor material 46 having dimensions of approximately 6"×9" is cut and has a rectangular heat zone border 48. The susceptor material 46 preferably is made of an aluminized polyester film or a steel coated polyester film bonded with adhesive to paper or paperboard. A similarly sized sheet of aluminized polyester film 50 is provided with a rectangular heat zone border 52 as seen in FIG. 9b. The aluminized polyester or steel coated film 50 is placed over susceptor material 46 where the heat zone borders 48 and 52 are bonded together with a heat sealer in order to make a pouch or container 8, as seen in FIG. 9c. Each heat zone border 48 is preferably free of the aluminum or steel coating of the susceptor 46 and is made of polyester, paper or paper coated with adhesive so that burning at the interfaces during sterilization. The cross-sectional view of the pouch 8 as seen in FIG. 9d shows that the top of the pouch with the aluminized or steel coated polyester film 50 is optically transparent while the bottom of the pouch that has the susceptor is optically opaque. Film 50 preferably is made of a polyester layer 54 having a thickness of approximately 1 mil which is joined to an interior aluminum layer 56 which has a thickness of approximately 150 nanometers. The opaque bottom preferably includes an interior aluminum layer 58 having a thickness of approximately 150 nanometers located on top of a polyester film 60 having a thickness of approximately 1 mil. The polyester film 60 is adhered via adhesive 62 to a paper outer layer 64 having a thickness of approximately 5 mils. Adhesive 62 is well known in the art and has a thickness of approximately 0.1 mils.

The pouch 8 was then placed in a laboratory microwave oven manufactured by Precision Scientific after first having heat sealed a dental explorer therein. The oven was set at a frequency of 2,450 MHz at a power of 240 watts so that the pouch 8 reached a temperature of 370° F. (188° C.) as monitored using a Luxtron temperature probe inside the pouch 8. The heating was continued for 7 more minutes while pulsing the power on and off to maintain an average temperature of 360° F. (182° C.). Upon removal from the oven the window was intact as was the rest of the pouch 8.

EXAMPLE 2

A rectangular pouch 8 having dimensions of 6"×9" is formed from a single sheet of susceptor material 46 that is folded to give a top 26 and a bottom 20 as shown in FIGS. 10a–b. A rectangular section 66 having dimensions of about 1 ½ "×4" is cut out of the center of the top 26 to form an opening. A rectangle of plain polyester film 68 having dimensions of about 2"×5" is placed inside the pouch 8 and is positioned to cover the opening. The film 68 is then bonded to the top 26 by a heat sealer.

A metallic dental explorer was heat sealed within the pouch and the entire pouch heated in the Precision Scientific oven set at 2,450 MHz at a power of 240 watts for 7 minutes. Once 350° F. (177° C.) was reached the power was pulsed on and off to maintain an average temperature of 260° F. (182° C.). After removal from the oven, the pouch 8 was examined and there were no signs of damage to the window or the susceptor, or the dental explorer due to arcing.

This reveals that windows can be made of different sizes to represent part of one or both sides, or an entire side of a pouch or rigid container 8.

Materials for the window can range from polyester to nylon films to other thin film optically transparent materials capable of withstanding temperatures of at least 400° F. As an alternative, the film may be coated with aluminum, steel or other material normally used to produce a susceptor, but without the paper backing. In this case, the film, when edge-bonded to the bottom susceptor will not only be structurally stable but will also heat, thereby aiding in the heating of the pouch.

Another feature of the container 8 which would be desirable is a visual indicator 70 as seen in FIG. 11 which illustrates when sterility has been achieved. This may be achieved with temperature sensitive inks or chemicals, commonly known in the industry, which integrate temperature and time, to provide a permanent marking or visual indicator of sterility. Thus, when the object 10 is sterilized a visual indicator, such as a color or the alpha-numeric indicia "STERILIZED" or "STERILIZATION," appear indicating that the object has received a sufficient of heat to be sterilized.

Another desirable feature of the container 8 is to insulate the outer surfaces so as to retain the heat created within the container. This can be done, for example, by placing an insulator layer 72 on a portion of or on the entire exterior surface 16 of container 8 as seen in FIG. 12. Insulator layer 72 may be made of a foam coating or a fibrous layer.

In another embodiment shown in FIG. 13, the container 8 may be a permanent or semi-permanent structure than disposable. In this case, a structure which may be constructed of a high heat plastic, for example, has a rigid microwave interactive layer 32 on its inner surface. The entire container would have a base and a cover which might be attached by a hinge on one side and provided with a lockdown or other sealing mechanism to maintain a hermetic seal during and after the heating cycle. Once closed and hermetically sealed, the cover and base define an interior space that contains one or more metallic surgical instruments 10. It may be necessary to provide a self-sealing valve to release pressure during heating. In this case, the container with tools therein is heated in the special low power microwave oven and, having reached sterility, is removed from the oven and maintained in a sealed fashion until the tools are needed by the dentist, doctor or other professional. Such a container may also be provided with a sterility indicator and temperature sensor.

The foregoing description is provided to illustrate the invention, and is not to be construed as a limitation. Numerous additions, substitutions and other changes can be made to the invention without departing from its scope as set forth in the appended claims. For example, container 8 may be used for other purposes, such as (1) containing and treating metallic materials with microwave radiation and (2) containing and cooking food items within a metallic vessel, like a pot or pan.

We claim:

1. A method of sterilizing a metal object, said method comprising the steps of:

providing a container with an exterior surface, said exterior surface comprises a microwave interactive layer and defines an interior space having an initial temperature;

placing said metal object within said interior space of said container;

exposing said microwave interactive layer to a first amount of microwaves so that the layer produces heat which raises the temperature within said interior space to a predetermined sterilization temperature;

sensing the temperature of said metal object within said interior space; and maintaining the temperature within said interior space at said predetermined temperature based on said sensed temperature for an amount of time sufficient to sterilize said metal object solely by said heat generated by said microwave interactive layer.

2. The method of claim 1, wherein said object is a dental instrument.

3. The method of claim 2, wherein said object is a medical instrument.

4. The method of claim 1, comprising the step of hermetically sealing said object within said interior space prior to applying said microwaves to said container.

5. The method of claim 1, wherein said microwave interactive material is flexible.

6. The method of claim 1, wherein said microwave interactive material is rigid.

7. The method of claim 1, wherein said predetermined sterilization temperature ranges from about 175° C. to about 200° C.

8. The method of claim 1, wherein said exposing step is performed during a period of time ranging from about 30 seconds to about 60 seconds.

9. The method of claim 1, wherein said amount of time sufficient to sterilize said object ranges from about 5 to 7 minutes.

10. The method of claim 1, said exposing step is performed by emitting said first amount of microwaves from a variable power microwave source that is operating at a maximum power level.

11. The method of claim 10, said maintaining step comprises reducing the power of said microwave source so as to maintain said predetermined temperature.

12. The method of claim 10, said maintaining step comprises pulsing the power of said microwave source so as to maintain said predetermined temperature.

13. The method of claim 12, wherein said period of said pulsed power ranges from about 1/30th of a second to about 20 seconds.

14. The method of claim 12, wherein the pulse width of said pulsed power ranges from about 1/60th of a second to about 10 seconds.

15. The method of claim 13, wherein the pulse width of said pulsed power ranges from about 1/60th of a second to about 10 seconds.

16. The method of claim 1, comprising the step of sensing the temperature of the surface of said container during said exposing step; and wherein said maintaining step is performed in response to the temperature sensed at the surface of said container.

17. The method of claim 1, comprising the step of sensing the temperature within the interior space of said container during said exposing step; and wherein said maintaining step is performed in response to the temperature sensed within the interior space of said container.

18. The method of claim 11, comprising the step of sensing the temperature of the surface of said container during said exposing step; and wherein said maintaining step is performed in response to the temperature sensed at the surface of said container.

19. The method of claim 11, comprising the step of sensing the temperature within the interior space of said container during said exposing step; and wherein said maintaining step is performed in response to the temperature sensed at the surface of said container.

20. The method of claim 18, wherein said reduction in power is in response to the temperature sensed at the surface of said container.

21. The method of claim 19, wherein said reduction in power is in response to the temperature sensed within the interior of said container.

22. The method of claim 12, comprising the step of sensing the temperature of the surface of said container during said exposing step; and wherein said maintaining step is performed in response to the temperature sensed at the surface of said container.

23. The method of claim 12, comprising the step of sensing the temperature within the interior space of said container during said exposing step; and wherein said maintaining step is performed in response to the temperature sensed within the interior space of said container.

24. The method of claim 22, wherein parameters of said pulsed power are controlled in response to the temperature sensed at the surface of said container.

25. The method of claim 24, wherein the period of said pulsed power is controlled in response to the temperature sensed at the surface of said container.

26. The method of claim 24, wherein the pulse width of said pulsed power is controlled in response to the temperature sensed at the surface of said container.

27. The method of claim 23, wherein parameters of said pulsed power are controlled in response to the temperature sensed within the interior space of said container.

28. The method of claim 27, wherein the period of said pulsed power is controlled in response to the temperature sensed within the interior space of said container.

29. The method of claim 27, wherein the pulse width of said pulsed power is controlled in response to the temperature sensed within the interior space of said container.

30. The method of claim 1, wherein said microwave interactive layer allows microwaves to be transmitted therethrough and interact with said metal object.

31. The method of claim 30, wherein said microwave interactive layer is constructed and arranged to allow microwaves to be transmitted therethrough and interact with said metal object during the exposing step, wherein the amount of microwaves interacting with said metal object during the exposing step is such that said metal object does not arc, spark or otherwise exhibit corona discharge during said exposing step.

32. The method of claim 30, wherein said microwave interactive layer is constructed and arranged to allow microwaves to be transmitted therethrough and interact with said metal object during the maintaining step, wherein the amount of microwaves interacting with said metal object during the maintaining step is such that said metal object does not arc, spark or otherwise exhibit corona discharge during said maintaining step.

33. The method of claim 31, wherein said microwave interactive layer is constructed and arranged to allow microwaves to be transmitted therethrough and interact with said metal object during the maintaining step, wherein the amount of microwaves interacting with said metal object during the maintaining step is such that said metal object does not arc, spark or otherwise exhibit corona discharge during said maintaining step.

34. The method of claim 1, wherein said initial temperature has a value approximately equal to said predetermined sterilization temperature.

35. The method of claim 34, wherein said object is a dental instrument.

36. The method of claim 34, wherein said object is a medical instrument.

37. The method of claim 33, comprising the step of hermetically sealing said object within said interior space prior to applying said microwaves to said container.

38. The method of claim 33 wherein said predetermined sterilization temperature ranges from about 175° C. to about 200° C.

39. The method of claim 33, wherein said amount of time sufficient to sterilize said object ranges from about 5 to 7 minutes 40. The method of claim 33, said exposing step is performed by emitting said first amount of microwaves from a variable power microwave source that is operating at a maximum power level.

41. The method of claim 40, said maintaining step comprises reducing the power of said microwave source so as to maintain said predetermined temperature.

42. The method of claim 40, said maintaining step comprises pulsing the power of said microwave source so as to maintain said predetermined temperature.

43. The method of claim 41, said maintaining step comprises pulsing the power of said microwave source so as to maintain said predetermined temperature.

44. The method of claim 33, comprising the step of sensing the temperature of the surface of said container during said exposing step; and
    wherein said maintaining step is performed in response to the temperature sensed at the surface of said container.

45. The method of claim 33, comprising the step of sensing the temperature within the interior space of said container during said exposing step; and
    wherein said maintaining step is performed in response to the temperature sensed within the interior space of said container.

46. The method of claim 41, comprising the step of sensing the temperature of the surface of said container during said exposing step; and
    wherein said maintaining step is performed in response to the temperature sensed at the surface of said container.

47. The method of claim 41, comprising the step of sensing the temperature within the interior space of said container during said exposing step; and
    wherein said maintaining step is performed in response to the temperature sensed at the surface of said container.

48. The method of claim 42, comprising the step of sensing the temperature of the surface of said container during said exposing step; and
    wherein said maintaining step is performed in response to the temperature sensed at the surface of said container.

49. The method of claim 42, comprising the step of sensing the temperature within the interior space of said container during said exposing step; and
    wherein said maintaining step is performed in response to the temperature sensed within the interior space of said container.

50. The method of claim 48, wherein parameters of said pulsed power are controlled in response to the temperature sensed at the surface of said container.

51. The method of claim 49, wherein the period of said pulsed power is controlled in response to the temperature sensed at the surface of said container.

52. The method of claim 34, wherein said microwave interactive layer is constructed and arranged to allow microwaves to be transmitted therethrough and interact with said metal object during the exposing step, wherein the amount of microwave interacting with said metal object during the exposing step in such that said metal object does not arc, spark or otherwise exhibit corona discharge during said exposing step.

53. A system for sterilizing a metal object, said system comprising:
    a microwave source emitting microwave radiation;
    a container positioned in said system so as to be exposed to said emitted microwave radiation, said container having an exterior surface which comprises a microwave interactive layer and defines an interior space having an initial temperature;
    a metal object located within said interior space of said container;
    a sensor that senses the temperature of said metal object located within said interior space and generates a signal representative of the temperature of said metal object; and
    a microwave source controller which receives said signal and controls the amount of microwaves that expose said microwave interactive layer based upon said signal so that the layer produces heat which raises the temperature within said interior space to a predetermined sterilization temperature which is maintained thereat for an amount of time sufficient to sterilize said metal object solely by said heat generated by said microwave interactive layer.

54. The system of claim 53, wherein said object is a dental instrument.

55. The system of claim 53, wherein said object is a medical instrument.

56. The system of claim 53, wherein said object is hermetically sealed within said interior space.

57. The system of claim 53, wherein said microwave interactive material is flexible.

58. The system of claim 53, wherein said microwave interactive material is rigid.

59. The system of claim 53, comprising a sensor connected to said microwave source that senses the temperature of the surface of said container and produces a signal representative of the temperature;
    wherein said signal is sent to said microwave source so as to control the emission of microwave radiation from said microwave source.

60. The system of claim 53, comprising a sensor connected to said microwave source that senses the temperature within the interior space of said container and produces a signal representative of the temperature;
    wherein said signal is sent to said microwave source so as to control the emission of microwave radiation from said microwave source.

61. The system of claim 53, wherein said microwave source produces pulsed emissions of microwave radiation.

62. The system of claim 61, comprising a sensor connected to said microwave source that senses the temperature of the surface of said container and produces a signal representative of the temperature;
    wherein said signal is sent to said microwave source so as to control the pulsed emissions of microwave radiation from said microwave source.

63. The system of claim 61, comprising a sensor connected to said microwave source that senses the temperature within the interior space of said container and produces a signal representative of the temperature;
    wherein said signal is sent to said microwave source so as to control the pulsed emissions of microwave radiation from said microwave source.

64. The system of claim 62, wherein the period of said pulsed emissions is controlled in response to the temperature sensed at the surface of said container.

65. The system of claim 62, wherein the pulse width of said pulsed emissions is controlled in response to the temperature sensed at the surface of said container.

66. The system of claim 63, wherein the period of said pulsed emissions is controlled in response to the temperature sensed at the surface of said container.

67. The system of claim 63, wherein the pulse width of said pulsed emissions is controlled in response to the temperature sensed at the surface of said container.

68. The system of claim 53, wherein said microwave interactive layer is constructed and arranged to allow microwaves to be transmitted therethrough and interact with said metal object.

69. The system of claim 68, wherein said microwave interactive layer is constructed and arranged so that the amount of microwaves transmitted through said microwave interactive layer is such that the transmitted microwaves interact with said metal object so that the metal object does not arc, spark or otherwise exhibit corona discharge.

70. The system of claim 53, wherein a portion of said exterior surface comprises a foil.

71. The system of claim 70, wherein said foil comprises a plurality of holes of such dimensions to permit the transmission of visible light without the transmission of microwave radiation.

72. The system of claim 53, wherein a portion of said exterior surface comprises a clear plastic film.

73. The system of claim 53, wherein a portion of said exterior surface comprises an insulator so as to retain the heat created within said interior space of said container.

74. The system of claim 53, wherein a portion of said exterior surface comprises a visual indicator which appears when the object has been sterilized.

75. The system of claim 74, wherein said visual indicator comprises indicia that appear when the object has been sterilized.

76. The method of claim 1, wherein said interior space is a substantially dry environment.

77. The method of claim 1, comprising the step of placing a second object within said interior space, wherein both objects within said interior space are metallic.

78. The method of claim 34, comprising the step of placing a second object within said interior space, wherein both objects within said interior space are metallic.

79. The system of claim 53, wherein said interior space is a substantially dry environment.

80. The method of claim 53, comprising a second object within said interior space, wherein both objects within said interior space are metallic.

* * * * *

UNITED STATES PATENT AND TRADEMARK OFFICE
CERTIFICATE OF CORRECTION

PATENT NO. : 5,552,112
DATED : September 3, 1996
INVENTOR(S) : Robert F. Schiffmann et al.

It is certified that error appears in the above-indentified patent and that said Letters Patent is hereby corrected as shown below:

On the Title Page

Under the heading "OTHER PUBLICATIONS", line 3, delete "Oburation" and substitute --Obturation--.

Under the heading "OTHER PUBLICATIONS", line 11, delete "Introduction" and substitute --Introducing--.

In the Claims

In claim 52, line 5, delete "microwave" and substitute --microwaves--.

In claim 52, line 6, delete "in" and substitute --is--.

Signed and Sealed this

Twenty-eighth Day of October, 1997

*Attest:*

BRUCE LEHMAN

*Attesting Officer*  *Commissioner of Patents and Trademarks*